(12) United States Patent
Hagberg et al.

(10) Patent No.: US 9,321,784 B2
(45) Date of Patent: Apr. 26, 2016

(54) HYDROGENATION OF ISOHEXIDE PRODUCTS FOR IMPROVED COLOR

(71) Applicant: ARCHER DANIELS MIDLAND COMPANY, Decatur, IL (US)

(72) Inventors: Erik Hagberg, Decatur, IL (US); Erin M. Rockafellow, Decatur, IL (US); Brennan Smith, Decatur, IL (US); Kenneth F. Stensrud, Decatur, IL (US)

(73) Assignee: Archer Daniels Midland Co., Decatur, IL (US)

( * ) Notice: Subject to any disclaimer, the term of this patent is extended or adjusted under 35 U.S.C. 154(b) by 0 days.

(21) Appl. No.: 14/437,266

(22) PCT Filed: Oct. 4, 2013

(86) PCT No.: PCT/US2013/063347
§ 371 (c)(1),
(2) Date: Apr. 21, 2015

(87) PCT Pub. No.: WO2014/070369
PCT Pub. Date: May 8, 2014

(65) Prior Publication Data
US 2015/0274745 A1  Oct. 1, 2015

Related U.S. Application Data

(60) Provisional application No. 61/720,457, filed on Oct. 31, 2012.

(51) Int. Cl.
*C07D 493/04* (2006.01)
(52) U.S. Cl.
CPC .................................... *C07D 493/04* (2013.01)

(58) Field of Classification Search
CPC ..................................................... C07D 493/04
See application file for complete search history.

(56) References Cited

U.S. PATENT DOCUMENTS 7,122,661 B2 * 10/2006 Fleche ................. C07D 493/04
536/124
2007/0173652 A1 * 7/2007 Holladay ............. C07D 493/04
549/416

OTHER PUBLICATIONS

Tinius Olsen. (c) 2011. Available from: < http://www.tiniusolsen.com/resource-center/psi-mpai.html >.*

* cited by examiner

*Primary Examiner* — Noble Jarrell
*Assistant Examiner* — John S Kenyon
(74) *Attorney, Agent, or Firm* — William B. Miller

(57) ABSTRACT

A process is described for making isohexides, comprising dehydrating one or more hexitols with an acid catalyst to form a crude dehydration product mixture including one or more isohexides, further processing the mixture to separate out one or more fractions of a greater purity or higher concentration of at least one of the isohexides, and hydrogenating at least one of a) the crude dehydration product mixture, b) a neutralized crude dehydration product mixture, following a neutralization of the crude dehydration product mixture, c) the product mixture following a neutralization step and further following a step to remove ionic species therefrom, d) a greater purity or higher concentration fraction, and e) a lesser purity or concentration fraction, by reaction with a hydrogen source in the presence of a hydrogenation catalyst. Hydrogenation improves the color and/or color stability of the material, especially of a finished isohexide product.

11 Claims, 5 Drawing Sheets

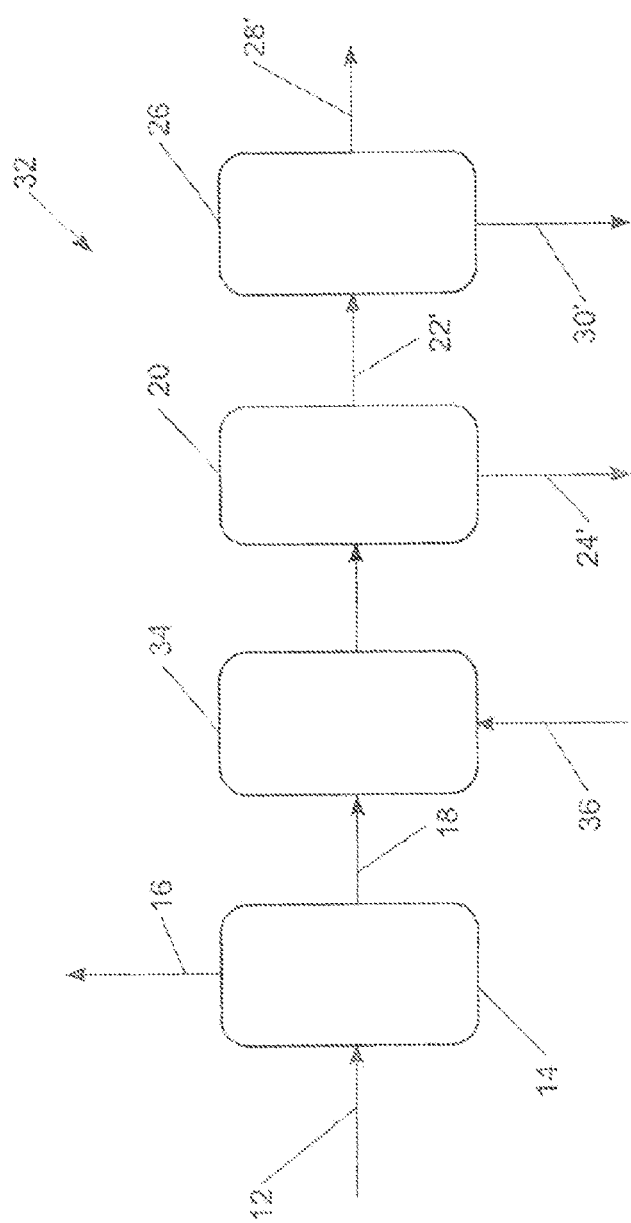

HYDROGENATION OF ISOHEXIDE PRODUCTS FOR IMPROVED COLOR

TECHNICAL FIELD

The present invention relates generally to methods for making an internal dehydration product of a sugar alcohol and to compositions including one or more such materials. The present invention relates also to compositions including these materials which can be described as having reduced color, and to the methods for making such reduced color compositions.

BACKGROUND ART

Sugar alcohols derived from six-carbon sugars (otherwise known as hexitols), such as, for example, sorbitol, mannitol, iditol and galactitol, have been long known. Particularly in recent years, significant interest has been expressed in the possible use of the internal dehydration products of such materials to displace petroleum-based materials in a number of commercially important applications. Dianhydrohexitols such as isosorbide, isomannide and isoidide, as made by the acid-catalyzed removal of two water molecules from the original internal structure of the corresponding hexitol, have been used or proposed for use in place of petroleum-based monomers such as terephthalic acid, for instance, though particularly in the case of isosorbide a substantial number of additional uses have been, are being or are envisaged to be developed.

As related in U.S. Pat. No. 7,122,661 and in U.S. Pat. No. 8,008,477, however, it has heretofore generally been required for the majority of these uses to apply a purification treatment to the compositions resulting directly from the dehydration step, as these compositions will typically contain each of the stereoisomers isosorbide, isomannide and isoidide, as well as less dehydrated materials such as sorbitan, mannitan and iditan, a variety of oxidation or degradation products, oligomeric and polymeric byproducts and various other "highly coloured species of a poorly defined nature", see, e.g., U.S. Pat. No. 8,008,477 at column 2, line 35.

As summarized in the aforementioned U.S. Pat. No. 7,122,661 and U.S. Pat. No. 8,008,477, a number of approaches had been suggested previously for obtaining the internal dehydration products (and particularly for obtaining the dianhydrohexitols such as isosorbide especially) in greater purity, for a variety of reasons. Some of these approaches sought improvements in purity through changes to the dehydration process by which the dianhydrohexitols are made, while other approaches involved a form of purification after the dianhydrohexitol compositions are formed.

For example, GB 613,444 describes the production of an isosorbide composition through dehydration carried out in a water/xylene medium, followed by distillation and recrystallization from an alcohol/ether mixture.

WO 00/14081 describes distillation and recrystallization from a lower aliphatic alcohol, or distillation alone in the presence of sodium borohydride and in an inert atmosphere.

U.S. Pat. No. 4,408,061 uses gaseous hydrogen halide or liquid hydrogen fluoride dehydration catalysts with carboxylic acid cocatalyst followed by distillation of the crude isosorbide or isomannide compositions thus obtained.

U.S. Pat. No. 4,564,692 briefly mentions prepurification on "ion exchangers and/or activated charcoal", followed, after concentration by evaporation and seeding of crystals of the desired isohexide, by crystallization from water.

Rather than modifying conventional acid-catalyzed dehydration methods or using different, often costly techniques to clean up the direct products of such methods as in the above references, it has also been proposed to generate the dianhydrohexitols by means of certain bimetallic catalysts in the presence of hydrogen. For example, EP 380,402 describes synthesis of the dianhydrohexitols by reacting sugar alcohols with hydrogen under pressure and in the presence of particular catalysts based on a combination of copper and a noble metal or gold.

U.S. Pat. No. 6,013,812 observes, however, that these catalysts tended to lose activity fairly rapidly, and proposes an improvement to a conventional acid-catalyzed dehydration wherein acid-stable Ru, Rh, Pd and/or Pt based hydrogenation catalysts and hydrogen are used during the dehydration step. The dehydration product is said to contain "less than 1 wt % polymers", col. 2, line 28.

U.S. Pat. No. 7,122,661 for its part describes a process for obtaining isohexide compositions of 99.5% or greater purity and having improved color and color stability on storage, without necessarily involving a comparatively costly and low yielding crystallization step from a solvent medium, through using an ion-exchange step followed by a decolorization treatment step. More particularly, a distilled isohexide composition is described as subjected to treatment with at least one ion-exchange means, which can be a mixed bed of anionic resin(s) and cationic resin(s) or a succession of cationic resin(s) and anionic resin(s), followed by treatment with at least one "decolorizing means". The decolorizing means can be activated charcoal in granular or pulverulent form. In certain embodiments, a second treatment with the decolorizing means is contemplated before the ion-exchange treatment step. Improved stability isosorbide compositions were said to be produced by the process, though the same steps—ion-exchange treatment followed by decolorizing means treatment—were surprisingly said to result in a destabilizing effect when performed in the reverse order.

U.S. Pat. No. 8,008,477, assigned to the same owner as the '661 patent and having one of the inventors of the '661 patent as its sole named inventor, describes an alternate process for preparing a color stable isosorbide composition. According to the '477 patent, the stability of an isohexide composition is not necessarily correlated with its purity, and preparation in an inert atmosphere and/or in the presence of sodium borohydride in the dehydration or in the distillation step likewise did not materially improve the stability of these compositions, col. 3, lines 58-67. Rather, "only" the use of specific stabilizing agents in nongaseous form and after the distillation step was helpful for improving the storage stability of isohexide compositions at ambient and moderate temperatures, col. 4, lines 1-14. Suitable "stabilizing agents" are chosen from the group comprising reducing agents, antioxidants, oxygen scavengers, light stabilizers, anti-acid agents, metal-deactivating agents and mixtures of at least any two of such materials, col. 4, lines 48-53. In certain embodiments, an optional further "purification step" was taught following the distillation, an example being the use of both ion exchange and decolorizing means of the type described in the earlier '661 patent.

JP 2006/316025 for its part earlier indicated that the formation of degradation/decomposition products in aged samples of isosorbide was related to auto oxidation of the 1,4-sorbitan monoanhydrohexitol side product and to unspecified "side reactions" involving a solvent (such as water and organic solvents such as xylene and toluene) from the dehydration of sorbitol to make isosorbide. The JP'025 reference prescribes multiple distillations of the crude isosorbide in the absence of a solvent at gradually increasing temperatures and/or at least one such solventless distillation followed by thermal treatment of the isosorbide to reduce the 1,4-sorbitan content of the isosorbide product, with bleaching of the isosorbide product included in each case by treating with ion exchange resins and carbon adsorption.

While the JP'025 reference does thus appreciate that degradation and color formation can proceed from the 1,4-sorbitan monoanhydrohexitol side product, neither the JP'025 reference nor the '477 patent appears to appreciate that the degradation pathways are as extensive as we have found or the corresponding degradation products and unstable intermediate species as numerous as we have found, as elaborated below. Not surprisingly, we have found that the approaches taken and the corrective measures proposed by the '477 patent and the JP'025 reference are correspondingly incomplete or even counterproductive.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this in mind, the present invention relates in one aspect to the use of a hydrogenation catalyst and hydrogen independent of and following an acid-catalyzed dehydration of one or more hexitols to improve the color of the whole or some portion of the products from the dehydration step. Performing the hydrogenation independently of the dehydration, rather than concurrently as contemplated in U.S. Pat. No. 6,013,812, others a number of advantages, as will be readily appreciated by those skilled in the art. For example, different catalysts and different conditions may be used, overall productivity may be improved in relation to catalyst and hydrogen requirements, certain portions of the product may be "treated" to a greater extent for premium applications and so forth.

In one embodiment, the hydrogenation is performed on the crude dehydration product mixture as a whole from the dehydration step. In one variant of this "whole dehydration product" embodiment, an inexpensive mineral acid is used for the acid-catalyzed dehydration, the entire dehydration product is neutralized through the addition of base, and the neutralized dehydration product containing salts undergoes hydrogenation at a first pressure. In another variant, the neutralized dehydration product is processed to remove ionic species therefrom before the hydrogenation step, and the hydrogenation is conducted at a second, lower pressure. In still another variant, the acid catalyst is selected such that the entire dehydration product can undergo hydrogenation and subsequent purification without first requiring a neutralization step.

In another embodiment, the crude dehydration product mixture from the dehydration step can be processed to separate out one or more parts or portions of greater purity or of a higher concentration of a given, desired product, for example, through distillation or chromatography, and some or all of these parts or portions can be subjected to hydrogenation. In a variant, less pure parts or portions that would otherwise have unacceptable color for any practical commercial application can also undergo hydrogenation, to provide a material with a sufficiently improved color to be acceptable in this respect for at least certain applications. Thus, for example, the overhead distillate from distillation of a crude isosorbide product mixture can undergo hydrogenation to provide a reduced color isosorbide product, while the bottoms can be hydrogenated as well to provide a marketable isosorbide bottoms product.

BRIEF DESCRIPTION OF THE DRAWINGS

FIGS. 2A and 2B are schematic diagrams of the process of FIG. 1, modified in accordance with certain embodiments of the present invention to include an hydrogenation step performed on a crude dehydration product mixture as a whole (FIG. 2A) or on one or both of the distillation overheads and bottoms following a distillation of a crude dehydration product mixture (FIG. 2B).

DESCRIPTION OF EMBODIMENTS

In a first aspect as just mentioned, the present invention concerns the use of a hydrogenation catalyst and hydrogen independent of and following an acid-catalyzed dehydration of one or more hexitols to improve the color of the whole or some portion of the products from the dehydration step.

Whereas the '477 patent indicates that the color stability of an isohexide composition is "not necessarily" related to its purity, and while the '477 patent contemplates a number of disparate types of "stabilizing agents", the reference contains very little discussion of the sources and mechanics of color formation and not many examples for or from within the disparate stabilizing agent types, from which the sources and mechanisms of color formation might possibly be inferred—sodium borohydride (described under "reducing agents"), morpholine (described under "antioxidants"), BHT (described under "antioxidants"), vitamin C (described under "antioxidants"), NaOH (described under "anti-acid agents"), $NaBO_2$ (described under "anti-acid agents") and $Na_2HPO_4$ (described under "anti-acid agents") comprising all of the exemplified additives providing compositions deemed "stable", having both a formic acid content of less than 5 ppm and an overall content of monoanhydrohexoses of less than 50 ppm, expressed on a dry weight basis relative to the dry weight of the composition as a whole. The earlier JP'025 reference does as mentioned earlier postulate that color formation on storage is related to the presence of the 1,4-sorbitan monoanhydrohexitol side product, but we have in fact identified a number of other materials in crude isosorbide product mixtures (beyond 1,4-sorbitan) that are related directly or indirectly to color formation in a conventional 100 percent molten finished product or in a conventional 85 weight percent solution product.

For the preparation of isosorbide from sorbitol by acid-catalyzed dehydration, these materials can include organic and inorganic salts, acids (for example, formic acid and levulinic acid), acid esters (e.g., sulfate esters from a sulfuric acid catalyzed dehydration step, phosphate esters from phosphoric acid catalyzed dehydration and in general the acid esters from a given oxygen acid catalyzed dehydration step) and their conjugate bases, furanics (e.g., 2-acetylfuran, 5-methylfurfural and various five carbon furanics), oligomeric and polymeric materials from, e.g., acid-catalyzed condensation of various ether functionalized impurities in a crude isosorbide product.

Figure 3:
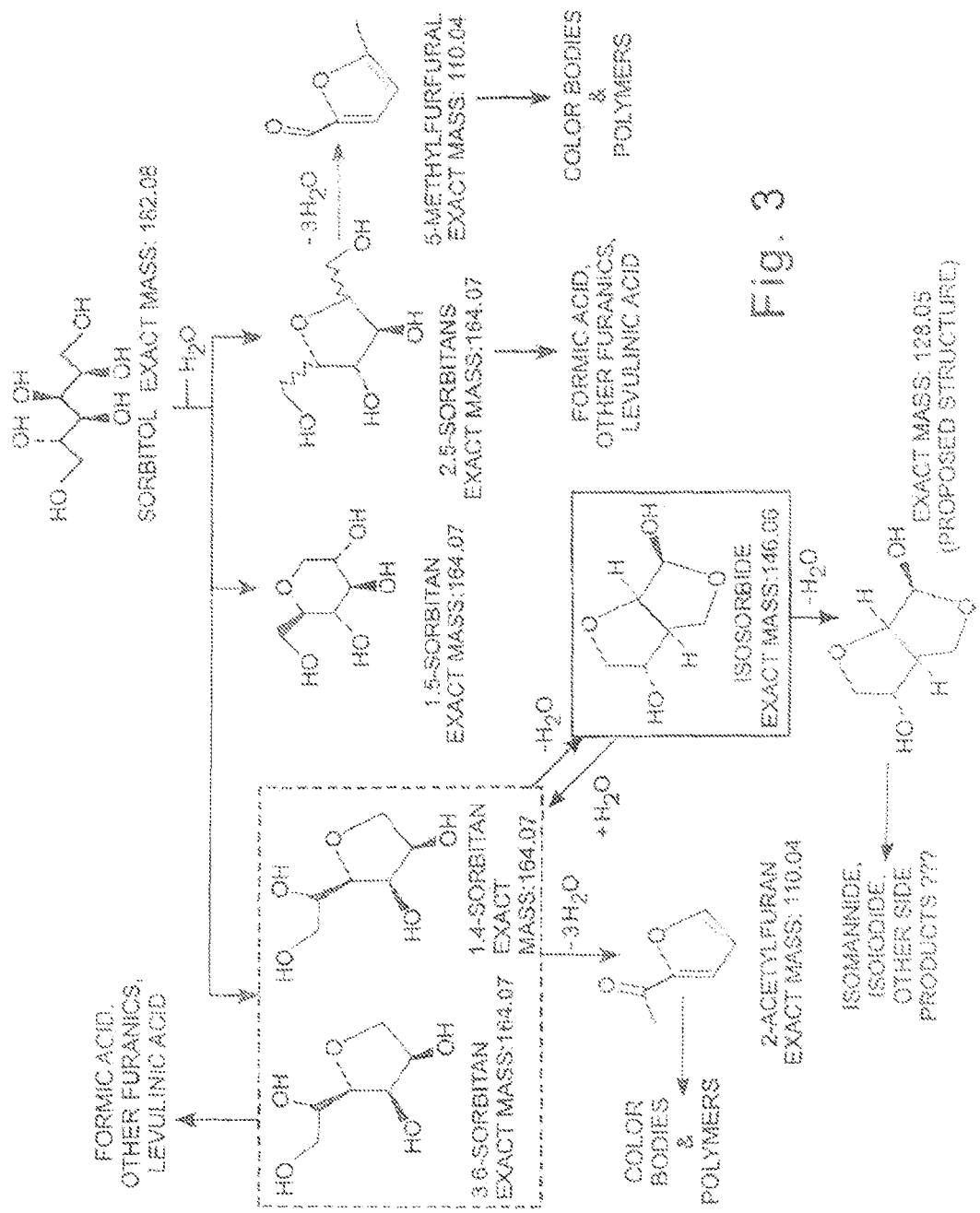
FIG. 3 depicts a proposed dehydration and degradation reaction pathway for a sulfuric acid-catalyzed dehydration of sorbitol, based on information obtained by liquid chromatography/mass spectroscopy, gas chromatography/mass spectroscopy and by ion chromatography of a crude dehydration product.

More particularly, without being bound and without limiting the present invention in any sense. FIG. 3 depicts a number of materials which have been identified or are believed to be present in the crude dehydration product mixture from a sulfuric acid-catalyzed dehydration of a commercially available sorbitol product and postulates the pathways by which these materials may be formed, based on the confirmed presence of compounds of a given molecular weight as indicated by gas chromatography/mass spectroscopy and, as to the specifically identified sulfate esters, by liquid chromatography/mass spectroscopy, as well as based on prior experience with the dehydration of sorbitol.

As will be evident to those skilled in the art on considering the complexity of the illustrated postulated pathways, not all materials present in the crude dehydration product mixture have been identified for FIG. 3 or even attempted to be identified nor quantified, and different (but generally similar) species can be expected in the dehydration of other hexitols by other processes or means than by the use of sulfuric acid. As well, upon distillation (or other further processing) of a crude dehydration product mixture of this character, still other compounds can be expected to form in varying degrees dependent on the particular distillation conditions employed, for example.

Further, while the materials present in a crude dehydration product mixture at a particular point in the overall process of making and finishing an isohexide product and/or while some of the compounds formed thereafter in a distillation step, in further processing or even after a certain time in storage may not result in unacceptable color, those skilled in the art will appreciate that ongoing chemical changes that occur in a particular finished isohexide product over a period of time under the storage conditions that can be expected to be experienced by the product, can nevertheless result with the passage of time in the development of unacceptable color in the finished isohexide product.

In any event, the sources and pathways by which color formation occurs in an isosorbide product are certainly more extensive and more numerous, respectively, than had previously been indicated by either the JP'025 reference or either of the '477 and '661 patents.

Figure 4:
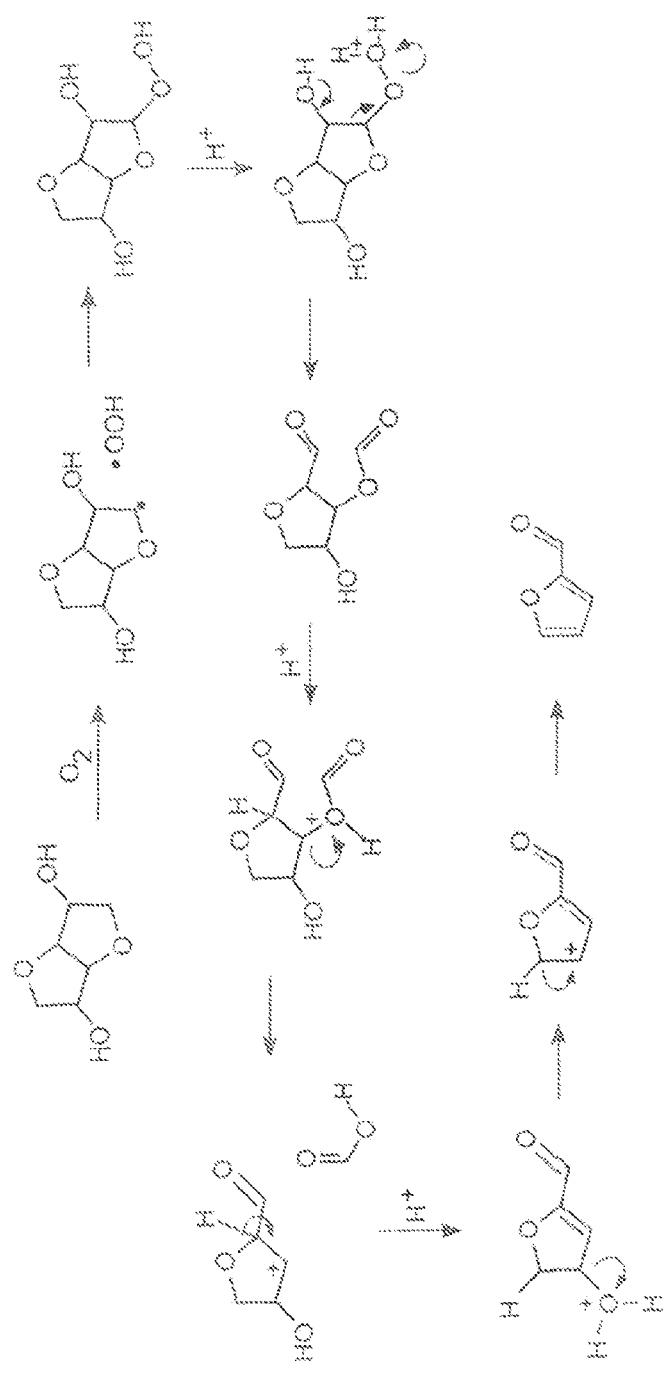
FIG. 4 depicts a proposed pathway for the auto-oxidation of isosorbide to produce furfural and formic acid.

With respect to the present invention, it was appreciated that more formic and other organic acids were being formed than could be accounted for by the sorbitans, and that these acids once formed would then catalyze a cascading series of dehydration reactions producing a variety of furanic, colored and unstable species. Without being limiting in any sense of the present invention, at least some of these are postulated to occur through an auto-oxidation mechanism; a proposed pathway is illustrated in FIG. 4 whereby on exposure to the oxygen in air over time isosorbide can degrade to form furfural as well as formic acid. While recognizing that the development of color over time in storage with exposure to air would not be prevented by such measures, nevertheless, owing to the high reduction potential of furans, it was considered that a catalytic hydrogenation could be helpful for producing a finished isohexide product having improved color as of its manufacture (hereinafter, "a reduced color product"). In fact, we have found not only that the crude isohexide product mixture could be hydrogenated to provide improved color prior to further processing to separate out one or more parts or portions of greater purity or of a higher concentration of a given, desired product, for example, through distillation or chromatography, but have also found that the various parts or portions could be hydrogenated individually after the further processing to improve the color of those parts or portions to an extent whereby additional, higher value uses of those parts or portions may be possible. For example, we have been able by means of the present invention to produce isosorbide distillation bottoms products having APHA color values of about 0, per ASTM D1209.

Parenthetically, we note here that we have also developed other useful measures for improving the color and/or the color stability of a finished isohexide product, for example, isosorbide, isomannide or isoidide; in certain embodiments as mentioned below, these other solutions are used in combination with the present invention. For example, where the finished isohexide product is stored in the presence of air for a period of time prior to use, a hydrogenated isohexide product or a reduced color part or portion as just described will experience an increase in color absent the inclusion of certain antioxidant additives; this increase in color may or may not be problematic for certain intended uses, so that a combination of the present invention and of the antioxidant additives may be indicated.

The manner in which the present invention may be employed can probably best be illustrated by reference to a known process for making an isohexide. As described above, a number of processes have been developed or proposed for making the isohexides/dianhydrohexitols/anhydrosugar alcohols from the corresponding sugar alcohols (and/or monoanhydrosugar alcohols). The manufacture of isosorbide from sorbitol has been particularly of interest. In addition to the processes described in the patents referenced above, commonly-assigned U.S. Pat. Nos. 6,849,748; 7,420,067; and 7,439,352 are examples of processes that have been developed for making isosorbide from sorbitol, and provide a useful, non-limiting context for describing the present invention.

Figure 1:
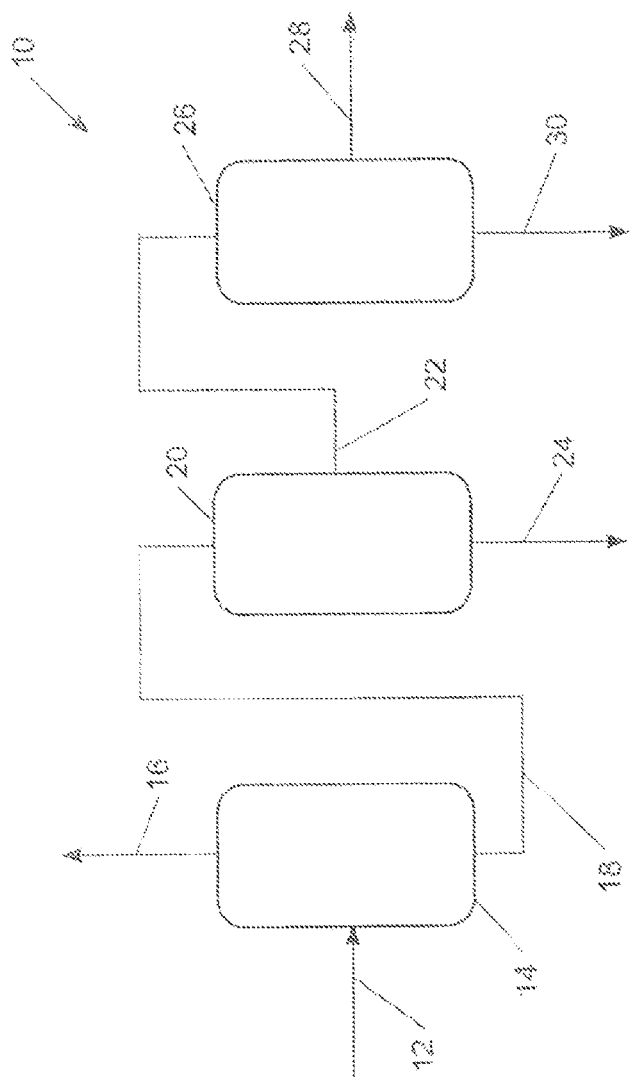
FIG. 1 is a schematic diagram of a process for manufacturing isosorbide from sorbitol in accordance with U.S. Pat. No. 7,439,352.

Turning now to FIG. 1, in a process 10 as originally described in the '352 patent, sorbitol is supplied as indicated by reference numeral 12 to reactor 14. The sorbitol 12 is first heated to a molten state, then is dehydrated in the reactor 14 in the presence of a catalyst for facilitating the dehydration to isosorbide, producing a water effluent 16 and a dehydration product mixture 18 including isosorbide. The dehydration product mixture 18 is then subjected to a first distillation in a first distillation apparatus 20 to form a first isosorbide distillate 22 and a first distillate bottoms 24. The first isosorbide distillate 22 is then subjected to a second distillation in a second distillation apparatus 26 to form a purified isosorbide product 28 and a second distillate bottoms 30.

More particularly, in the first step of the process 10 of FIG. 1, the sorbitol is melted by standard methods that are known in the art. For example, the sorbitol can be melted by placing it in a 3-neck round bottom flask equipped with an agitator, temperature probe, and vacuum line. Preferably, the sorbitol is heated to at least 100 degrees Celsius to 200 degrees Celsius. For sorbitol powder, to provide a specific example, the preferred melting temperature is from 98 degrees Celsius to 105 degrees Celsius while an even more preferred melting temperature is from 98 degrees Celsius to 100 degrees Celsius. Once molten, the sorbitol is subject to stirring.

A catalyst that will facilitate the dehydration of the sorbitol is then added to the molten starting material. Typically acid catalysts have been used to facilitate the dehydration of sugar alcohols such as sorbitol, including for example soluble acids, acidic ion exchange resins, and inorganic ion exchange materials. Sulfuric acid, phosphoric acid, p-toluenesulfonic acid, and p-methanesulfonic acid are given as examples of preferred soluble acids that may be used, though one of skill in the art would recognize that other soluble acids with similar properties would be useful as well.

Zeolite powders are examples of inorganic ion exchange materials that could be used; specifically an acidic zeolite powder such as a type ZSM-5 ammonium form zeolite powder may be used. Examples of zeolite powders said to be useful include, but are not limited to, CBV 3024 or CBV 5534G (both available from Zeolyst International), and/or T-2665 or T-4480 (both available from United Catalysis, Inc.). One of skill in the art would recognize that other zeolite powders with similar properties may be useful though not specifically listed here.

A sulfonated divinylbenzene/styrene co-polymer acidic ion exchange resin provides an example of a possible acidic ion exchange resin catalyst. Examples include, but are not limited to, AG50W-X12 from BioRad Laboratories, Amberlyst 15 or Amberlyst 35 from Rohm & Haas, RCP21H from Mitsubishi Chemical Corp., and Dowex 50Wx5 (Dow Chemical Co.). The sulfonated divinylbenzene/styrene co-polymer acidic ion exchange resin, Amberlyst 35, is indicated as a particularly preferred resin for the production of isosorbide from sorbitol. One of skill in the art would be aware of other acidic ion exchange resins with similar properties that could be used.

The amount of catalyst used is indicated as generally being on the order of from (0.01 equivalents to 0.15 equivalents by weight. A preferred amount of catalyst is 0.1 equivalents by weight.

The dehydration can be carried out under a vacuum, at elevated temperatures, and with stirring of the reaction mixture. The vacuum can range over a pressure of from 0.05 Torr to 40 Torr, with preferred pressures of from 1 Torr to 10 Torr. As a specific example, a preferred pressure for the dehydration of sorbitol to isosorbide is from 1 Torr to 10 Torr. The temperature for the dehydration can be from 90 deg. C. to 140 deg. C. In certain embodiments, the dehydration temperature can be from 98 deg. C. to 130 deg. C. especially, from 120 degrees Celsius to 130 degrees Celsius. The dehydration can be carried out over a period of approximately 2 hours at such temperatures. The water can be pulled off of the melted sorbitol/catalyst mixture under a vacuum of from 1 Torr to 10 Torr. The dehydration reaction is preferably performed in a reactor which can run in a batch or continuous mode. In embodiments wherein the acid catalyst is a solid acid catalyst (e.g., acidic ion exchange resin), the reactor can preferably hold or contain baskets to which the solid acid catalyst can be added.

Following the dehydration procedure, the resultant dehydration product mixture 18 is purified. In one embodiment, a vacuum distillation is used. In a more specific embodiment, the vacuum distillation is performed using a film evaporator, specifically a wiped film evaporator. One example of a wiped film evaporator apparatus that is useful in the present invention is a vertical agitated thin-film processor. Advantages of using a wiped film evaporator include handling of viscous solutions, improved product purity, and low residence time, which leads to a reduction or elimination of product degradation. Specifically with respect to production of isosorbide from sorbitol, use of a wiped film evaporator was said to provide approximately an 80% yield on distillation, negligible water loss during distillation (which results in reduced polymerization), and to provide for further recovery of isosorbide and sorbitan from the residue. The distillation process results in a first isosorbide distillate 22.

The pot temperature and vacuum used for the first distillation apparatus 20 can vary, but vapor temperatures of from 140 degrees Celsius to 190 degrees Celsius are preferred. More preferred vapor temperatures are from 160 degrees Celsius to 170 degrees Celsius, especially from 165 degrees Celsius to 170 degrees Celsius. The vacuum pressure can be from 0.05 Torr to 40 Torr, preferably being from 1 Torr to 10 Torr. For the vacuum distillation of isosorbide, a vacuum pressure of from 1 Torr to 10 Torr, a pot temperature of 180 degrees Celsius, and a vapor temperature of from 160 degrees Celsius to 170 degrees Celsius are said to be most preferred. Alternative purification methods such as filtration or the addition of activated charcoal with subsequent crystallization are also mentioned as useful.

The first isosorbide distillate 22 is then preferably subjected to a second vacuum distillation in a second distillation apparatus 26, for example, by means of a second wiped film evaporator. The second wiped film evaporator can be of the same type as, or different than, the first wiped film evaporator. The conditions (e.g., vacuum pressure and temperature) of the second vacuum distillation can be the same as, or different than, the conditions of the first vacuum distillation, the parameters of which are described above. The use of two film evaporators allows for production and purification of isosorbide without the use of potentially harmful organic solvents.

In an alternate embodiment described in the '352 patent, the first isosorbide distillate 22 is subjected to melt crystallization wherein the first isosorbide distillate 22 is heated until molten (isosorbide's melting point is about 65 degrees Celsius), and then cooled over time until the crystallization point is reached, but not so much that the material solidifies. In fact, a slurry-like consistency is preferred, so that the material can be centrifuged. As used herein, the term "slurry-like consistency" refers to a material that is a mixture of liquid with several finely divided particles. The centrifugation is performed at a relatively high speed for a relatively short period of time in order to avoid solidification of the material, and also to avoid having the desired isosorbide product drawn off with the impurities. For example, the centrifugation can be performed at 3000 to 4000 rpm for 5 minutes, though those skilled in the art will appreciate that the duration of centrifugation will ideally vary depending on the amount of material to be purified. The resultant isosorbide in any case is indicated as being at least 98% pure, and in most cases being greater than 99% pure (depending upon the solidity of the "slurry").

Alternatively, the '352 patent also contemplates that the first isosorbide distillate 22 can be subjected to solvent recrystallization. Solvents mentioned as useful include, but are not limited to, acetone, ethyl acetate, and low molecular weight alcohols such as ethanol and methanol.

In still another embodiment mentioned in the '352 patent, further purification of the first isosorbide distillate 22 can involve subjecting the first distillate 22 to a solvent wash, followed by filtration. Preferably, the solvents are cold, for example, having a temperature of 0 degrees Celsius to 23 degrees Celsius. Solvents mentioned included acetone, ethyl acetate, and low molecular weight alcohols such as ethanol and methanol. Filtration was described as carried out by means well known in the art.

In one embodiment 32 of a process according to the present invention, shown schematically in FIG. 2A, a process according to any of the aforementioned embodiments described in U.S. Pat. No. 7,439,352 is modified to include the addition of an hydrogenation step 34 carried out on the crude dehydration product mixture 18 before the first distillation apparatus 20. In hydrogenation step 34, hydrogen 36 (or a source of hydrogen, more generally) is supplied for carrying out an hydrogenation of the mixture 18 in the presence of an hydrogenation catalyst.

Figure 2B:
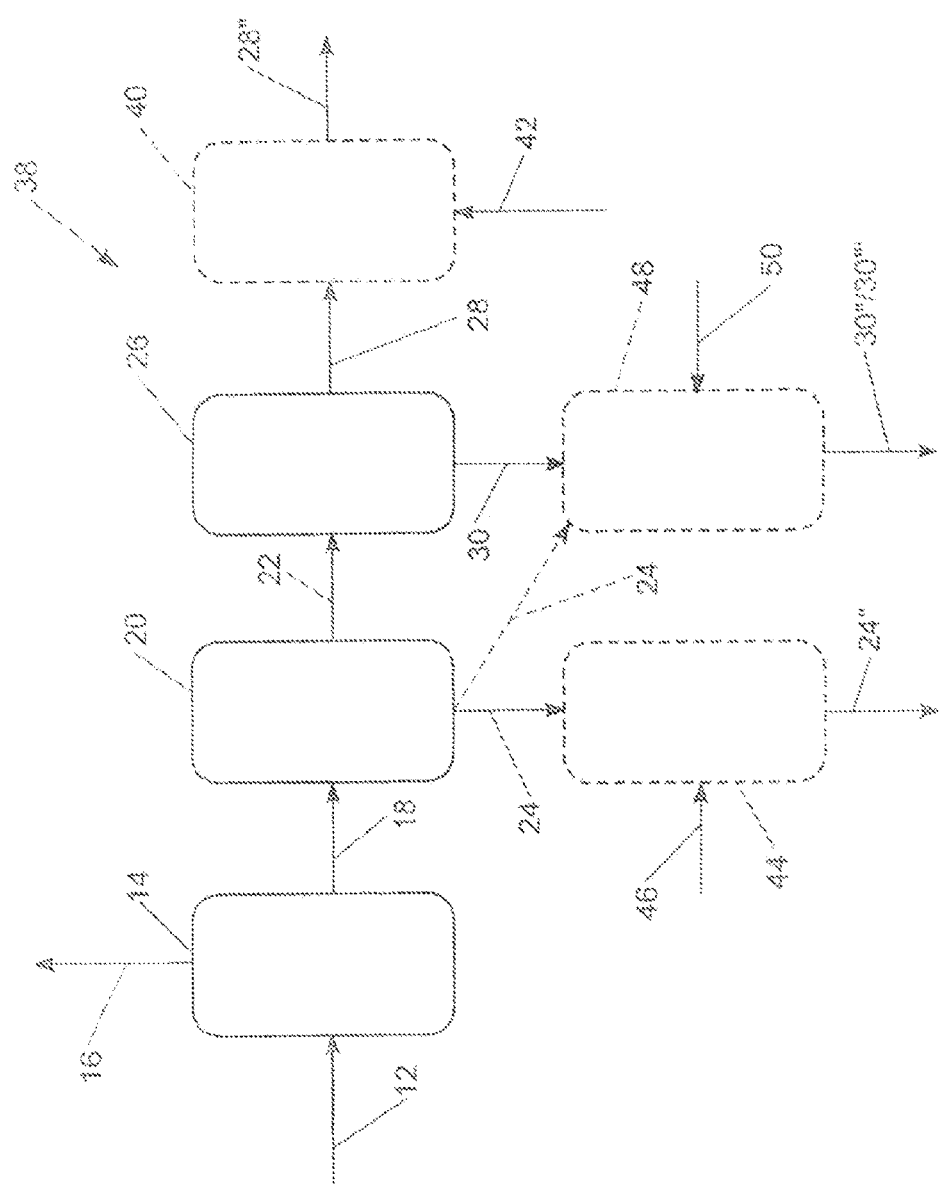

In an alternate scheme 38 shown schematically in FIG. 2B, the crude dehydration product mixture 18 as a whole is not hydrogenated but is passed to first distillation apparatus 20 as in the '352 patent, and fractions from either or both of the first distillation apparatus 20 and the second distillation apparatus 26 are instead hydrogenated.

In one embodiment, the purified isosorbide product 28 is hydrogenated in hydrogenation step 40 with hydrogen 42 in the presence of an hydrogenation catalyst, to provide a purified isosorbide product 28" with improved color.

In another embodiment, the first distillate bottoms 24 is hydrogenated in a step 44 with hydrogen 46 in the presence of an hydrogenation catalyst, to provide a modified first distillate bottoms 24' having reduced color.

In yet another embodiment, the second isosorbide distillate bottoms 30 is hydrogenated in step 48 by hydrogen 50 supplied in the presence of a hydrogenation catalyst, under conditions effective for carrying out the hydrogenation. A modified second distillate bottoms 30" is produced having reduced color.

In still another option, both of the first and second distillate bottoms 24 and 30 can be hydrogenated together to produce a modified combined distillate bottoms product (30''') having reduced color.

In yet another variation, all of the first distillate bottoms 24, the second distillate bottoms 30 and the purified isosorbide product 28 can be hydrogenated independently of one another, by hydrogenating any two of these in combination as well as hydrogenating the third independently or by combining and hydrogenating all of these together.

What constitutes a sufficient improvement in color for any given material obviously can vary dependent on the color requirements of different purchasers and users, on the end uses or applications to which the improved materials will be put and on the initial quality of the material—which will vary according to the different methods and conditions under which the materials have been produced. In general, however, it is expected that finished 100% molten isohexide products made at least in part by means of the present invention (in combination with one or both of the inventions described in the commonly-assigned, concurrently filed applications as needed) will demonstrate an APHA color as determined in accordance with ASTM D1209 of 100 or less, preferably 20 or less, more preferably 15 or less and especially 10 or less. In a conventional 85% solution product form, finished isohexide products will preferably demonstrate an APHA color of 100 or less, preferably 20 or less, more preferably 15 or less, and especially 10 or less.

In some instances an isohexide product may be realized through the use of hydrogenation alone that fully meets the color and color stability on storage requirements applicable to that product and a contemplated end use scenario, while in other circumstances either or both of the additional measures described below may be combined with the use of hydrogenation to achieve desired color and color stability on storage requirements. In any event, it is considered that one skilled in the an will be well able to determine the solution or combination of solutions needed to most economically and efficiently accomplish a needed reduction in color and a requisite color stability on storage under conventionally encountered storage conditions, for any given isohexide product and end use.

Thus, in certain embodiments, an impurity removal system including the use of ion exclusion, ion exchange or both as described in commonly-assigned U.S. Patent Application Ser. No. 61/720,453 filed Oct. 31, 2012 for "IMPROVED METHOD OF MAKING INTERNAL DEHYDRATION PRODUCTS OF SUGAR ALCOHOLS", can be employed preferably upstream of an hydrogenation step according to the present invention. Preferably such an impurity removal system removes substantially all of at least the ionic species from the crude dehydration product mixture 18 and more preferably substantially all of the aforementioned species or precursors of such species tending to give rise to color formation in a finished isohexide product on storage. Hydrogenation demand in such circumstances can be expected to be considerably reduced, consistent with a supplemental or polishing role for hydrogenation as to color-forming species or precursors of such species.

In other embodiments, one or more antioxidant additives as described in commonly-assigned U.S. Patent Application Ser. No. 61/720,466, which was filed Oct. 31, 2012 for "ADDITIVES FOR IMPROVED ISOHEXIDE PRODUCTS", can be added to a crude dehydration product mixture (or a hydrogenated crude dehydration product mixture) before the same is further processed to ultimately yield a finished, improved storage stability product enriched in the desired isosorbide material compared to the crude dehydration product mixture 18, or to yield a reduced color, improved storage stability part or portion (e.g., a bottoms fraction). Preferred antioxidants identified therein for color-stabilizing isosorbide were hindered phenols containing one or more methoxyl groups and no other functional groups, other than alkyl groups. Examples of such preferred antioxidants for color-stabilizing conventional 100% molten and 85% solution isosorbide products include di-tert-butyl-4-methoxyphenol (or DTMP, (CAS 128-37-0), butylated hydroxyanisole (BHA, mix of 2- and 3-tert-butyl-4-hydroxyanisoles, CAS 25013-16-5), 2,6-dimethoxy-4-methylphenol (DMMP, CAS 6638-05-7) and 2,6-dimethoxyphenol (DMP, CAS 91-10-1). Of these, most preferred are BHA and DMMP.

Returning now to the hydrogenation step specifically, any hydrogenation catalyst and any set of process conditions that will effectively reduce furanic species of the character shown in FIG. 3 may be used, though as a general matter, heterogeneous hydrogenation catalysts are preferred as are relatively higher hydrogen pressures (for example, between 6.9 and 13.8 MPa, gauge (1000 to 2000 psig)). Supported platinum, palladium and ruthenium catalysts and certain conditions are used in the examples below, but those skilled in the art will be familiar with a variety of other hydrogenation catalysts and the conditions appropriate to their use.

As will be evident from the examples following, hydrogenations conducted at comparatively higher and lower hydrogen pressures have provided different results when applied to materials at certain stages of a process and that have been processed in a particular manner, so that lower hydrogen pressures (for example, less than 6.9 MPa, gauge (1000 psig) and preferably not more than 4.1 MPa, gauge (600 psig)) may be sufficient in certain embodiments while in other embodiments higher hydrogen pressures may be indicated. Thus, in the particular embodiment wherein hydrogenation is performed on the crude dehydration product mixture as a whole, wherein an inexpensive mineral acid has been used for the acid-catalyzed dehydration and the entire dehydration product has been neutralized through the addition of base, the hydrogenation is preferably conducted at higher pressure hydrogen conditions. Where the neutralized dehydration product has been processed to first remove ionic species therefrom before the hydrogenation step, the hydrogenation can be conducted with lower pressure hydrogen especially where further processing (to provide a finished isohexide product) is undertaken at modest temperature conditions. In any event, those skilled in the an will be well able to determine without undue experimentation what hydrogenation conditions will be required to achieve a certain reduction in color, given the examples that follow.

The present invention is further illustrated by the following examples:

Example 1

A once-distilled isosorbide product (102.72 g, having a measured APHA color according to ASTM D1209 of 106), a commercial 5% ruthenium on carbon hydrogenation catalyst (3.05 g), and 500 mL of deionized water were added to a 1 L stainless steel autoclave reactor. The vessel was purged three times by pressurizing to 3.5 MPa (500 psi) with hydrogen and then venting. The vessel was then again pressurized to 3.5 MPa (500 psi) with hydrogen, heated to 120 degrees Celsius and stirred for 4 hours. After cooling and venting the reactor, the catalyst was removed by filtering the solution through a #5 Whatman filter paper. The water was then removed by rotary evaporator, and the remaining solid was dried in a 40 degrees Celsius vacuum oven. The product was a white crystalline solid with a reduced APHA color of 51. A trace of the carbon supported catalyst remained in the sample.

Samples of this isosorbide were heated at 70 degrees Celsius for 24 hrs. After heating, the samples were diluted to 25% solids and the APHA color was measured. The APHA colors were then normalized to 100% solids based on the actual measured concentration of the solutions. Results are in Table 1 as follows.

TABLE 1

| Sample | Temperature (deg C.) | Time (hrs) | APHA Color |
|---|---|---|---|
| Once distilled | — | 0 | 106 |
| Once distilled | 70 | 24 | 112 |
| Hydrogenated once distilled | — | 0 | 51 |
| Hydrogenated once distilled | 70 | 24 | 50 |

Example 2

Once-distilled isosorbide (120.27 g, APHA 106), a commercial 5% ruthenium on carbon (3.51 g) hydrogenation catalyst, and 600 mL of deionized water were added to a 1 L stainless steel autoclave reactor. The vessel was purged three times by pressurizing to 3.5 MPa (500 psi) with hydrogen and then venting. The vessel was then again pressurized to 3.5 MPa (500 psi) with hydrogen, then heated to 120 deg C. and stirred for 4 hrs. After cooling and venting the reactor, the catalyst was removed by filtering the solution through a 0.2 micrometer disposable filter. The water was then removed with a rotary evaporator, and the remainder was dried in a 40 deg C. vacuum oven. The product was a white crystalline solid with an APHA color of 51. No obvious catalyst remained in the sample.

Samples of the isosorbide were heated at 70 degrees Celsius for 24 hrs. After heating, the samples were diluted to 25% solids and the APHA color was measured again. The APHA colors were then normalized to 100% solids based on the actual measured concentration of the solutions. Isosorbide samples prepared from triple recrystallized material were heated at 70 degrees and APHA measurements taken at the same intervals, for comparison. Results are reported in Table 2:

TABLE 2

| Sample | Time (days) | Temp. (deg C.) | APHA Color |
|---|---|---|---|
| Single Distilled | 0 | — | 106 |
|  | 1 | 70 | 112 |
|  | 3 | 70 | 134 |
|  | 7 | 70 | 107 |
|  | 14 | 70 | 90 |
| Hydrogenated Single Distilled | 0 | — | 51 |
|  | 1 | 70 | 50 |
|  | 3 | 70 | 63 |
|  | 7 | 70 | 71 |
|  | 14 | 70 | 58 |
| Triple Recrystallized | 0 | — | 25 |
|  | 1 | 70 | 17 |
|  | 3 | 70 | 17 |
|  | 7 | 70 | 25 |
|  | 14 | 70 | 32 |

Example 3

A stainless steel, 1 L Parr reactor vessel was charged with 100 g of singly distilled isosorbide, 200 mL of water and 5 grams of a commercial 10% Pd/C hydrogenation catalyst. The vessel was then fastened to a floor stand reactor and pressurized to 1.4 MPa (200 psi) hydrogen after three successive purges with 3.5 MPa (500 psi) hydrogen. The mixture was heated to 100 deg C. with mechanical stirring at 1100 rpm for 4 hours. After this time, the heterogeneous matrix was passed through a 0.22 um Millipore filter and dewatered. The crystalline product tested 96.1% pure isosorbide and was determined to have an APHA value of 116.

Example 4

A stainless steel, 1 L Parr reactor vessel was charged with 100 g of crude isosorbide (pH 9), 200) mL of water and 5 grams of a commercial 10% Pd/C hydrogenation catalyst. The vessel was then fastened to a floor stand reactor and pressurized to 1.4 MPA (200 psi) hydrogen after three successive purges with 3.5 MPa (500 psi) hydrogen. The mixture was heated to 100 deg C. with mechanical stirring at 1100 rpm for 6 hours. After this time, the heterogeneous matrix was passed through a 0.22 um Millipore filter, dewatered, and short path, pot-distilled in an oil bath with temperature of 180-190 degrees Celsius at less than 1 torr. Approximately 20 grams of a colorless, crystalline material (35%) was collected, which was analyzed as 97.5% pure isosorbide and determined to have an APHA value of 39. A distillation temperature increase to 195-205 degrees Celsius caused more isosorbide to distill, but the distillates collected invariably manifested an intense yellow color.

Example 5

A stainless steel, 1 L Parr reactor vessel was charged with 100 g of crude isosorbide (pH 9), 200 mL of water and 10 grams of a commercial 10% Pd/C hydrogenation catalyst. The Parr reactor vessel was then fastened to a floor stand reactor and pressurized to 1.4 MPa (200 psi) hydrogen after three successive purges with 3.5 MPa (500 psi) hydrogen. The mixture was heated to 100 deg C. with mechanical stirring at 1100 rpm for 4 hours. After this time, the heterogeneous matrix was passed through a 0.22 um Millipore filter, dewatered, and short path, pot-distilled in an oil bath with temperature of 180-190 degrees Celsius at less than 1 torr. Approximately 18 grams of a colorless, crystalline solid was collected, which was analyzed as 95.8% pure and determined to have an APHA value of 46. A distillation temperature increase to 195-205 degrees Celsius resulted in more isosorbide distilling over, but the distillates collected invariably manifested an intense yellow color.

Example 6

A stainless steel, 1 L Parr reactor vessel was charged with 100 g of crude isosorbide (pH 9), 200 mL of water and 5 grams of a commercial 0.5% Pd/C hydrogenation catalyst. The vessel was then fastened to a floor stand reactor and pressurized to 3.5 MPa (500 psi) hydrogen after three successive purges with 3.5 MPa (500 psi) hydrogen. The mixture was heated to 100 degrees Celsius with mechanical stirring at 1100 rpm for 4 hours. After this time, the heterogeneous matrix was passed through a 0.22 um Millipore filter, dewatered, and short path, pot-distilled in an oil bath with temperature of 180 to 190 degrees Celsius at less than 1 torr. Approximately 22 grams of a colorless, crystalline solid (39%) was collected, which was analyzed as 95.9% pure isosorbide and determined to have an APHA value of 66. A distillation temperature increase to 195-205 degrees Celsius recovered more isosorbide, but the distillates collected invariably manifested an intense yellow color.

Example 7

A stainless steel, 1 L Parr reactor vessel was charged with 100 g of crude isosorbide that had not been neutralized (having a pH of about 1), 200 mL of water and 5 grams of a commercial 5% Pt/C hydrogenation catalyst. The vessel was then fastened to a floor stand reactor and pressurized to 3.5 MPa (500 psi) hydrogen after three successive purges with 3.5 MPa (500 psi) hydrogen. The mixture was heated to 100 degrees Celsius with mechanical stirring at 1100 rpm for 4 hours. After this time, the heterogeneous matrix was passed through a 0.22 um Millipore filter and dewatered. The resulting, viscous mixture manifested a light bluish tinge, and was found to have an APHA value of 67. Short path, pot-distillation in an oil bath with a temperature of 180-190 degrees C. at less than 1 torr produced approximately 17 grams of a colorless, crystalline solid (30%), which was analyzed as 97.5% pure isosorbide and determined to have an APHA value of 50. A distillation temperature increase to 195-205 degrees Celsius recovered more isosorbide, but as in previous examples, the distillates collected invariably manifested an intense yellow color.

Example 8

A stainless steel, 1 L Parr reactor vessel was charged with 100 g of crude isosorbide that had not been neutralized (with a pH of about 1), 200 mL of water and 10 grams of a 10% Pd/C catalyst. The vessel was then fastened to a floor stand reactor and pressurized to 3.5 MPa (500 psi) hydrogen after three successive purges with 3.5 MPa (500 psi) hydrogen. The mixture was heated to 100 degrees Celsius with mechanical stirring at 1100 rpm for 2 hours. After this time, the heterogeneous matrix was passed through a 0.22 um Millipore filter then tandem 150 cc columns packed with strong acid cation and strong base anion exchange resins. The resulting matrix, after dewatering, exhibited an intense yellow color. Short path, pot-distillation in an oil bath with temperature of 155 to 165 degrees Celsius at less than 1 torr produced approximately 30 grams of a colorless, crystalline solid (71%), which was analyzed as 98.4% pure and determined to have an APHA value of 33. An increase in the oil bath temperature to 190 to 195 degrees Celsius produced additional material, but in contrast to previous examples, the distillate collected remained highly pure and colorless (with APHA values less than 30).

Example 9

100 grams of neutralized, crude isosorbide was passed through tandem 150 cc columns packed with the same strong acid cation and strong base anion exchange resins. The resulting, yellowish matrix was then dewatered, producing a viscous ion-exchanged crude isosorbide mixture. A stainless steel, 1 L Parr reactor vessel was charged with 100 g of this material, 200 mL of water and 10 grams of a 10% Pd/C hydrogenation catalyst. The vessel was then fastened to a floor stand reactor and pressurized to 3.5 MPa (500 psi) hydrogen after three successive purges with 3.5 MPa (500 psi) hydrogen. The mixture was heated to 100 degrees Celsius with mechanical stirring at 1100 rpm for 2 hours. After this time, the heterogeneous matrix was passed through a 0.22 um Millipore filter then again through tandem 150 cc column packed strong acid cation and strong base anion exchange resins. The resulting matrix, after dewatering, exhibited an intense yellow color. Short path, pot-distillation in an oil bath at temperatures of from 155 to 165 degrees Celsius at <0.1 torr produced approximately 33 grams of a colorless, crystalline solid (59%), which was analyzed as 97.5% pure isosorbide and determined to have an APHA value of 36. The oil bath temperature was then increased to 190-195 degrees Celsius, and the distillate collected was highly pure and colorless (APHA values less than 30).

Example 10

100 grams of neutralized, crude isosorbide was added to 200 mL of absolute ethanol and stirred for 1 hour. A profusion of solid matter was observed after this time, which was removed from the mixture by vacuum filtration. The residual, darkly colored matrix was concentrated and short-path distilled in an oil bath with temperature maintained at from 165 to 175 degrees Celsius at less than 1 torr, producing approximately 28 grams of a yellowish crystalline solid (50%), that analyzed as 97.7% pure isosorbide and was determined to have an APHA value of 129.

For comparison, 100 grams of neutralized, crude isosorbide was added to 200 mL of absolute ethanol and stirred for 1 hour. A profusion of solid matter was observed after this time, which was removed from the mixture by vacuum filtration. The dark brown solution in this instance was then charged to a stainless steel, 1 L Parr reactor vessel, along with 10 g of a commercial 10% Pd/C hydrogenation catalyst. The vessel was then fastened to a floor stand reactor and pressurized to 3.5 MPa (500 psi) hydrogen after three successive purges with 3.5 MPa (500 psi) hydrogen. The mixture was heated to 100 degrees Celsius with mechanical stirring at 1100 rpm for 4 hours. After this time, the light yellow heterogeneous matrix was passed through a 0.22 um Millipore filter, dewatered, and short path, pot-distilled in an oil bath with a temperature maintained between 155 and 165 degrees Celsius at less than 1 torr. Approximately 31 grams of a colorless, crystalline material (55%) was collected, which was analyzed as 98.9% pure isosorbide and determined to have an APHA value of 13. To cause more isosorbide to distill, the oil bath temperature was increased to 190-195 degrees Celsius. The additional distillate collected was highly pure and colorless (APHA values less than 30). The bottoms manifested an intense yellow color.

Example 11

156 g of neutralized, crude isosorbide (having a pH of 8.5, and an APHA color in excess of 5000) was dissolved in 156 g of water. After complete dissolution, the homogeneous mixture was added to a 1 L stainless steel Parr vessel. Fifteen grams of a 10% Pd/C catalyst was weighed out and added to the vessel, which was then fastened to a floor stand reactor. Three sequential 6.9 MPa (1000 psi) purges with hydrogen were executed to ensure that most of the remaining air in the vessel headspace was removed. The vessel was then pressurized to 9.0 MPa (1300 psi) with hydrogen, mechanical stirring commenced at 1100 rpm, and the heating jacket activated to heat the reactor to 100 degrees Celsius. Once this temperature was attained, the reaction proceeded for 4 hours. After this time, the reaction mixture was cooled to room temperature and excess catalyst removed off using a 0.22 micron filter. The clear, colorless solution was then concentrated with a rotary evaporator under high vacuum until about 95% of the water had been removed. Quantitative analysis of the mixture revealed that no isosorbide had degenerated (about 41% of the mixture, as before). APHA analysis, conducted in triplicate, manifested a color of 0 for the high pressure hydrogenated crude isosorbide. Approximately fifty grams of this material was then distilled using a short path, pot distillation apparatus under vacuum (with a bath temperature of 190 degrees Celsius at less than 5 torr pressure), affording purified isosorbide that analyzed as 96% pure and that had an APHA color of 10.

Example 12

150 g of crude isosorbide (APHA=1791) that had previously been passed through tandem strong acid cation exchange and strong base anion exchange columns, was dissolved in 150 g of water. After complete dissolution, the homogeneous mixture was added to a 1 L stainless steel Parr vessel. Fifteen grams of a 10% Pd/C catalyst was weighed out and added to the vessel, which was then fastened to a floor stand reactor. Three sequential 6.9 MPa (1000 psi) purges with hydrogen were executed to ensure that most of the remaining air in the vessel headspace was removed. The vessel was then pressurized to 9.0 MPa (1300 psi) with hydrogen, mechanical stirring was initiated at 1100 rpm, and the heating jacket activated to heat the reactor vessel to 100 degrees Celsius. Once this temperature was achieved, the reaction proceeded for 4 hours. After this time, the reaction mixture was cooled to room temperature and residual catalyst removed with a 0.22 micron filter. The clear, colorless solution was then concentrated with a rotary evaporator under high vacuum until about 95% of the water had been removed. Quantitative analysis of the mixture revealed that no isosorbide had decomposed. APHA analysis of the hydrogenated ion exchanged crude mixture, conducted in triplicate, confirmed a color of 0. Approximately 50 grams of this material was then distilled using a short path, pot distillation apparatus under vacuum (using a bath temperature of 190 degrees Celsius, less than 5 torr pressure), providing isosorbide at 99% purity and whose APHA color was less than 1.

Example 13

About 150 grams of light brown, viscous isosorbide bottoms from a thin film distillation of a neutralized, ion exchanged (strong acid cation then strong base anion-exchanged) crude isosorbide product mixture were dissolved in about 150 grams of water. After complete dissolution, the homogeneous mixture was added to a 1 liter stainless steel Parr vessel. About 15 grams of a commercial 10% Pd/C hydrogenation catalyst was then added. Following three sequential 6.9 MPa (1000 psi) purges with hydrogen, the Parr reactor was pressurized to 9.0 MPa (1300 psi) with hydrogen, mechanical stirring was commenced and the heating jacket activated to heat to a reaction temperature of 100 degrees Celsius. After 4 hours, the reactor contents were cooled to room temperature and the catalyst removed by filtration as in previous examples. The filtrate was observed to be colorless, and after being concentrated by use of a rotary evaporator, the APHA color of the viscous hydrogenated bottoms product was determined (in triplicate) to be 0. The starting APHA color of the isosorbide bottoms (neat) had been 1200.

Example 14

About 150 grams of isosorbide bottoms from a short path pot distillation of a neutralized crude isosorbide product mixture (that in contrast to Example 13 had not been ion exchanged and thus contained salts from the neutralization) were dissolved in about 150 grams of water. After complete dissolution, the homogeneous mixture was added to a 1 liter stainless steel Parr vessel. About 15 grams of a commercial 10% Pd/C hydrogenation catalyst was then added. Following three sequential 6.9 MPa (1000 psi) purges with hydrogen, the Parr reactor was pressurized to 9.0 MPa (1300 psi) with hydrogen, mechanical stirring was commenced and the heating jacket activated to heat to a reaction temperature of 100 degrees Celsius. After 4 hours, the reactor contents were cooled to room temperature and the catalyst removed by filtration as in previous examples. The filtrate was observed to be colorless, and after being concentrated by use of a rotary evaporator, the APHA color of the viscous hydrogenated bottoms product was determined (in triplicate) to be 0. The starting APHA color of these salt-containing isosorbide bottoms (neat) had been, in comparison to the ion-exchanged isosorbide bottoms of Example 13, greater than 5000.

The invention claimed is:

1. A process for making one or more isohexides, comprising:
    dehydrating one or more hexitols in the presence of an acid catalyst to form a crude dehydration product mixture including one or more isohexides;
    after the dehydration step, further processing the crude dehydration product mixture to separate out one or more fractions of a greater purity or higher concentration of at least one of the isohexides in the crude dehydration product mixture and one or more fractions of a lesser purity or concentration; and
    hydrogenating one or both of
        a greater purity or higher concentration fraction and
        a lesser purity or concentration fraction following the further processing of the crude dehydration product mixture,
    by reaction with a hydrogen source in the presence of a hydrogenation catalyst, under conditions effective to carry out the hydrogenation.

2. The process according to claim 1, wherein the further processing includes distillation, and further wherein a bottoms product from the distillation is hydrogenated.

3. The process according to claim 1, wherein the further processing includes distillation, and further wherein a greater purity or higher concentration fraction is hydrogenated.

4. The process according to claim 3, wherein the further processing includes thin film or short path distillation.

5. The process according to claim 2, wherein the further processing includes thin film or short path distillation.

6. The process according to claim 1, further comprising the step of removing ionic species from the crude dehydration product mixture prior to the further processing step, by contacting the crude dehydration product mixture with one or more ion exchange resins, through ion exclusion means or through a combination of ion exchange and ion exclusion means.

7. The process according to claim 2, further comprising the step of removing ionic species from the crude dehydration product mixture prior to the further processing step, by contacting the crude dehydration product mixture with one or more ion exchange resins, through ion exclusion means or through a combination of ion exchange and ion exclusion means.

8. The process according to claim 7, wherein the further processing includes thin film or short path distillation.

9. The process according to claim 3, further comprising the step of removing ionic species from the crude dehydration product mixture prior to the further processing step, by contacting the crude dehydration product mixture with one or more ion exchange resins, through ion exclusion means or through a combination of ion exchange and ion exclusion means.

10. The process according to claim 9, wherein the further processing includes thin film or short path distillation.

11. The process of claim 1, wherein the acid catalyst is a soluble acid catalyst.

* * * * *